| United States Patent [19] | [11] | 4,279,859 |
|---|---|---|
| Gutcho et al. | [45] | Jul. 21, 1981 |

[54] SIMULTANEOUS RADIOASSAY OF FOLATE AND VITAMIN $B_{12}$

[75] Inventors: Sidney Gutcho, Monsey; Lillian Mansbach, New City, both of N.Y.

[73] Assignee: Becton Dickinson & Company, Paramus, N.J.

[21] Appl. No.: 919,387

[22] Filed: Jun. 26, 1978

Related U.S. Application Data

[60] Division of Ser. No. 817,563, Jul. 21, 1977, Pat. No. 4,146,602, which is a continuation-in-part of Ser. No. 762,992, Jan. 27, 1977, abandoned.

[51] Int. Cl.³ .................. B65D 71/00; G01N 33/48
[52] U.S. Cl. ........................... 422/61; 424/1; 424/12; 23/230 B
[58] Field of Search ............. 424/1, 12; 23/230 B

[56] References Cited

U.S. PATENT DOCUMENTS 4,146,602  3/1979  Gutcho et al. .................. 424/1

*Primary Examiner*—Benjamin R. Padgett
*Assistant Examiner*—Christine M. Nucker
*Attorney, Agent, or Firm*—Louis E. Marn; Elliot M. Olstein

[57] ABSTRACT

A serum sample is heated at an alkaline pH to release folate and vitamin $B_{12}$ from endogenous binders. A simultaneous radioassay for folate and vitamin $B_{12}$ is effected by contacting the sample with binder for folate, binder for vitamin $B_{12}$, folate labeled with one radioactive isotope and vitamin $B_{12}$ labeled with another radioactive isotope, followed by separation of bound and free portions, and determination of the radioactivity of at least one of the portions. The amounts of folate and vitamin $B_{12}$ present in the sample may be determined from standard curves.

67 Claims, No Drawings

SIMULTANEOUS RADIOASSAY OF FOLATE AND VITAMIN $B_{12}$

This is a division of application Ser. No. 817,563, filed July 21, 1977, U.S. Pat. No. 4,146,602, which is a continuation in part of U.S. application Ser. No. 762,992, filed on Jan. 27, 1977, now abandoned.

This invention relates to radioassay, and more particularly, to a radioassay for folate and vitamin $B_{12}$.

Currently, endogenous folate is measured by a competitive protein-binding technique. In brief, competitive protein-binding (CPB) for the assay of folate involves the ability of unlabeled folate in serum or other media to complete with labeled folic acid for a specific folate binder, present in usable concentrations in such sources as cow's milk, hog kidney, etc., and thereby inhibit the binding of labeled folic acid. As a result of the competitive inhibition, the ratio of bound labeled folic acid to free labeled folic acid diminishes as the concentration of unlabled folate is increased. Accordingly, the concentration of folate in an unknown sample; e.g., a patient's serum, is obtained by comparing the inhibition observed with that produced by known amounts of folate, as presented in a standard curve.

Endogenous vitamin $B_{12}$ is also determined by a similar competitive protein-binding technique, with the vitamin $B_{12}$ binder generally being hog intrinsic factor.

The present invention is directed to an improved radioassay wherein the folate and vitamin $B_{12}$ present in a sample may be determined simultaneously.

In accordance with the present invention, a sample containing folate and vitamin $B_{12}$ is contacted with a binder for the folate, a binder for the vitamin $B_{12}$, a folate tracer labeled with a first radioactive isotope and a vitamin $B_{12}$ tracer labeled with a second radioactive isotope different from the first radioactive isotope, resulting in competitive binding between the labeled and unlabeled folate and the labeled and unlabeled vitamin $B_{12}$ for their respective binder sites. The bound portions of labeled and unlabeled folate and bound portions of labeled and unlabeled vitamin $B_{12}$ are simultaneously separated from the unbound portions of labeled and unlabeled folate and unbound portions of labeled and unlabeled vitamin $B_{12}$, followed by counting the radioactivity of at least one of the bound or unbound portions, with the amounts of folate and vitamin $B_{12}$ then being determined from standard curves.

In accordance with the present invention, folate and vitamin $B_{12}$ are released from their endogenous binders by heating a sample, containing folate and vitamin $B_{12}$; e.g., a serum or plasma sample, with the endogenous binders being desroyed by such heating. The heating can be effected at a wide variety of pH values, with the pH generally being 5 or greater. The pH is most generally at least 7.0 (neutral or alkaline pH), with the pH preferably being at least 9.0 and preferably no greater than 9.6. The most preferred pH is from 9.2 to 9.4 (generally 9.3) in that this permits the release to be effected at the same pH as the subsequent assay in which folic acid is employed as a standard, instead of the reduced methyl derivative of folic acid. The heating to release vitamin $B_{12}$ and folate from their binders is generally effected at a temperature of from about 95° C. to about 110° C., and preferably of from about 98° C. to about 105° C.

The release of folic acid and vitamin $B_{12}$ from their endogenous binders is also effected in the presence of a suitable reducing agent in order to preserve the endogenous folate present in the serum in reduced form. The reducing agent which is included during the heating step is a reducing agent which maintains the reduced folate without adversely affecting the vitamin $B_{12}$ and which is stable under the assay conditions. As representative examples of suitable reducing agents there may be mentioned: ascorbate, Cleland's reagen (dithiothreitol); dithioerythritol; monothioglycol; thiodiglycol; thioglycollic acid; cysteine; homocysteine; gluthathione; mercaptoethanol; sulfhydryl reducing agents; inorganic reducing agents, such as sodium sulfite; sodium dithionite; sodium sulfide, sodium metabisulfite, with the organic reducing agents being preferred.

After release of folic acid and vitamin $B_{12}$ from their endogenous binders and destruction of such endogenous binders, the sample is contacted with a dual tracer; i.e., a tracer for folate and a tracer for vitamin $B_{12}$, and a dual binder; i.e., a binder for folate and a binder for vitamin $B_{12}$. The receptors, both naturally occurring and antibodies, for folate are well known in the art, and any one of such receptors may be employed in the assay of the present invention. As representative examples of such receptors, there may be mentioned: receptors or binders extracted from various animal organs particularly kidneys and pancreas; $\beta$-lactoglobulin preparations; cow's milk, dolphin serum and the like, with milk binder being preferred. Similarly, binders or receptors for vitamin $B_{12}$ are known in the art, e.g., saliva, chicken serum, intrinsic factor, with the preferred binder being intrinsic factor.

The folate tracer is either folic acid (pteroylmonoglutamic acid) (PGA) [or the reduced 5-methyl derivative of folic acid, 5-methyltetrahydrofolic acid (MTFA)] or appropriate analogs thereof, labeled with a radioactive isotope, which is preferably a radioactive isotope of iodine. The term folate tracer generically refers to radiolabeled folic acid, the radiolabeled reduced 5-methyl derivative and the radiolabeled analogs thereof. The 5-methyl derivative is generally not employed as a tracer as a result of the instability thereof. The radiolabeled folate employed as a tracer is preferably radiolabeled folic acid, and the term radiolabeled folic acid includes the radiolabeled analogs thereof: i.e., folic acid substituted with a radiolabeled radical. The preferred radioactive isotope is a radioactive isotope of iodine, and most preferably $I^{125}$ with the tracer being a folic acid including a substituent which includes a radioiodinated phenol or imidazole group such as histidine, histamine, tyrosine or tyramine, which is substituted with a radioactive isotope of iodine. A particularly preferred tracer is one in which the $\alpha$-carboxyl group of the glutamyl moiety is substituted with radioiodinated tyrosyl or histidyl, as disclosed in U.S. Application Ser. No. 727,408, filed Sept. 29, 1976 hereby incorporated by reference; however, it is to be understood that the tracer can also be one in which the $\gamma$-carboxyl group is so substituted, as disclosed in U.S. Pat. No. 3,989,812.

The vitamin $B_{12}$ tracer is preferably a radiolabeled vitamin $B_{12}$, with the vitamin $B_1$ preferably being labeled with $^{57}Co$.

In accordance with the preferred procedure, the assay is effected at an alkaline pH; i.e., the assay and release of folate and vitamin $B_{12}$ from binders are both effected at alkaline pH, with the release being effected at temperatures known in the art; i.e., generally in the order of from about 98° C. to 105° C. It is to be understood that the release and subsequent assay could be effected at different pH values; however, identical pH values are preferably employed in that this eliminates the necessity for a pH adjustment.

In accordance with the most preferred procedure for effecting the assay, folate and vitamin $B_{12}$ are released from their endogenous binders at an alkaline pH in the order of from about 9.2 to 9.4 followed by effecting to assay at a pH of from about 9.2 to about 9.4 with the folate tracer being in the form of a radioiodinated folic acid, with the radioiodinated folic acid preferably being a radioiodinated analog of folic acid; e.g., radioiodo-substituted histidyl, tyrosyl or tyramyl, preferably tyrosyl. The tracer for vitamin $B_{12}$ is $^{57}Co$ labeled vitamin $B_{12}$. The use of radiolabeled folic acid and assay of endogenous folates at such a pH permits the use of folic acid as a standard, instead of MTFA, as described in U.S. Pat. No. 3,988,431.

It is to be understood that in accordance with the preferred procedure wherein folic acid is employed as a standard, even though the assay should be effected at pH 9.2—9.2, the release from binder can be effected at another pH value. Similarly, if the standard for the assay is MTFA, the assay and/or release can be effected at pH values other than 9.2-9.4.

The bound and unbound portions are separated by procedures known in the art, with such portions generally being separated by the use of a particulate adsorbent. The preferred adsorbent is dextran-coated charcoal; however, it is to be understood that any one of a wide variety of other adsorbents, such as ion exchange resins, inorganic adsorbents, etc., may be employed for separating the bound and free portions. In addition, the assay may be effected by a so-called solid phase assay technique, wherein the receptors for folate and vitamin $B_{12}$ are previously coated on or bound to a solid support, such as a test tube, or insoluble polymer, whereby the bound and free portions may be readily separated from each other. The techniques for effecting separation of bound and free portions, whether by the addition of a particulate adsorbent, or by the use of a receptor bound to a solid phase, forms no part of the present invention.

After separation of the bound and free portions, the radio-activity of either the bound or free portion or both portions is determined, and the determined radioactivity is compared with a standard curve, by procedures known in the art. As should be apparent, since different radioactive isotopes are employed for labeling the folate tracer and vitamin $B_{12}$ tracer, the respective tracers may be counted in different channels of a counter or if the counter has one channel, it can be calibrated so that different counter settings will count one isotope at a time.

The invention will be further described with respect to the following example; however, the scope of the invention is not to be limited thereby.

EXAMPLE

The following reagents are used in the dual assay:
1. Dual Tracer
   1.5$\mu$ Ci $\alpha$—(pteroylglutamyl)$^{125}$I-L-tyrosine (prepared as described in U.S. Application Ser. No. 727,408) and 0.75$\mu$ Ci vitamin $B_{12}[^{57}Co]$, human serum albumin, sodium borate, dextran and preservatives.
2. Dual Binder
   Folate binder from bovine milk and hog intrinsic factor, both formulated for a trace binding (Bo) of 55±15%, human serum albumin, dextran and preservatives.
3. Dual Standards containing human serum albumin, sodium borate, sodium chloride and preservatives.
   3A Dual Standard A Zero level
   3B Dual Standard B 1.0 ng/ml Folic acid; 100 pg/ml $B_{12}$
   3C Dual Standard C 2.0 ng/ml Folic acid; 200 pg/ml $B_{12}$
   3D Dual Standard D 4.0 ng/ml Folic acid; 400 pg/ml $B_{12}$
   3E Dual Standard E 10 ng/ml Folic acid; 1000 pg/ml $B_{12}$
   3F Dual Standard F 20 ng/ml Folic acid; 2000 pg/ml $B_{12}$
4. Buffer pH 9.3, 0.05 M sodium borate with 6.25 $\mu$g potassium cyanide/ml.
5. Cleland's Reagent (dithiothreitol) solution, 5%.
   5A. Assay Buffer
   A mixture of 1 ml of Reagent 5 to 50 ml of Reagent 4.
6. Dextran-coated charcoal suspension, 4.4±0.1 g dextran-charcoal dry mix (1:10), suspending agent and sodium chloride in 100 ml sterile distilled water.

| PROTOCOL | |
|---|---|
| Preparation of a Standard Curve | Clinical Determinations |
| 1. Number 16 polypropylene tubes sequentially from 1–16. | 1. Starting with 17, consecutively number two polypropylene tubes for each clinical sample. |
| 2. Add assay Buffer (Reagent 5A) as follows: | 2. Add 1000$\mu$ 1 Assay Buffer (Reagent 5A) to each tube |
| Tubes   Buffer | |
| 1,2      1000$\mu$ 1 | |
| 3–16    1000$\mu$ 1 | |
| 3. Add Dual Standards (Reagents 3A–3F) as follows: | 3. Add 100$\mu$ 1 patient sample to each of two tubes. Mix gently. |

| Tube No. | Standard | Folic Acid as mg/ml | Vitamin $B_{12}$ as mg/ml |
|---|---|---|---|
| 3–6 | 100$\mu$ 1A | 0 | 0 |
| 7,8 | 100$\mu$ 1B | 1.0 | 100 |
| 9,10 | 100$\mu$ 1C | 2.0 | 200 |
| 11,12 | 100$\mu$ 1D | 4.0 | 400 |
| 13,14 | 100$\mu$ 1E | 10 | 1000 |
| 15,16 | 100$\mu$ 1F | 20 | 2000 |

Mix gently.
4. Cover all tubes loosely with plastic caps (except 1 and 2).
5. Heat all tubes (except 1 and 2) in a glycerin or water bath at 100° C. for 45 minutes.
6. Remove all tubes from 100° C. bath. Cool to 20°-25° C. in a running water bath. Do not continue assay until the tubes are within this range. Uncap all tubes.

| 7. Add 100$\mu$ 1 Dual Tracer (Reagent 1) to all tubes. Mix gently by hand. Set tubes 1 and 2 aside at room temperature until Step 15. | 7. Add 100$\mu$ 1 Dual Tracer (Reagent 1) to each tube. Mix gently by hand. |
|---|---|
| 8. Add 100$\mu$ 1 Dual Binder (Reagent 2) to tubes 5–16. Mix gently by hand. | 8. Add 100$\mu$ 1 Dual Binder (Reagent 2) to each tube. Mix gently by hand. |

From this point, all tubes are treated as follows:

9. Incubate at room temperature for 45 minutes from the time of the last addition of the binder. Cover the rack of tubes with aluminum foil to exclude light or keep in the dark.
10. Add 0.4 ml dextran-coated charcoal to tubes 3-16 and to all patient sample tubes (17, 18, etc.). Do not add to tubes 1 and 2. This reagent is "squirted" into each tube to obtain a uniform suspension in the reaction mixture.
11. Keep at room temperature for 10 minutes from the time of last addition in Step 10.
12. Centrifuge at a minimum of $1240 \times g$ for 15 minutes, preferably in the cold. Shorter times may be sufficient in equipment of higher centrifuge force.
13. Consecutively number a set of clean tubes, beginning with 3.
14. Gently decant each clear supernatant into the similarly numbered tube prepared in Step 13. Maximal transfer is obtained by hitting the rims together. Avoid decanting over any charcoal to the counting tube. Discard the charcoal residues.
15. Count the radioactivity in the supernatants and tubes 1 and 2 in sequence for one or more minutes with a scintillation (gamma) counter.

If the counter has two or more channels it should be calibrated to count [$^{125}$I] in one channel and [$^{57}$Co] in another channel. If the counter has one channel it should be calibrated so that different counter settings will count one isotope at a time. In the case of the latter, it will be necessary to count the tubes twice, once setting the counter for [$^{125}$I] and obtaining the folate curve counts and sample counts, then setting the counter for [$^{57}$Co] to obtain the Vitamin B$_{12}$ curve counts and sample counts. If in counting one isotope there is spillover from the other isotope, counter adjustments must be made. Decreasing channel widths can minimize or eliminate such spillover.

The folate curve and values are calculated from the counts obtained by counting [$^{125}$I]; the vitamin B$_{12}$ curve and values are obtained by counting [$^{57}$Co].

As the radioactive tracer decays with age, increased counting times may be required. (This will be unnecessary with efficient equipment). The volume of tracer used must be that specified in this protocol; tracer volume should not be increased to compensate for decay. Binding of each vitamin to its respective binder remains essentially unchanged with time using the volume of tracer specified. Reproducible results will be obtained by following the protocol which has been described.

The Standard Curve covers the range of 1.0 to 20 ng/ml folate and 100 to 2000 pg/ml of Vitamin B$_{12}$. A "Blank" (tubes 3 and 4) is used to correct for background counts and radioactive tracer which is not adsorbed onto the charcoal.

The present invention is particularly advantageous in that it is possible to effect a simultaneous assay for folate and vitamin B$_{12}$. Moreover, in accordance with the particularly preferred embodiments, Applicant unexpectedly found that vitamin B$_{12}$ and folate can both be effectively released from their endogenous binders and effectively assayed at an alkaline pH.

Numerous modifications and variations of the present invention are possible in light of the above teachings, and therefore, within the scope of the appended claims, the invention may be practiced otherwise than as particularly described.

What is claimed is:

1. A reagent kit for use in effecting a simultaneous assay for folate and vitamin B$_{12}$ in a sample containing both substances but free of endogenous binder therefor, wherein said sample is contacted with a binder for the folate, a binder for the vitamin B$_{12}$, a folate tracer labeled with radioiodine, and a vitamin B$_{12}$ tracer labeled with radiocobalt and the radioactivity of at least one of the bound and unbound portions is counted to determine both folate tracer and vitamin B$_{12}$ tracer, said reagent kit comprising:
   a binder for the folate and a binder for the vitamin B$_{12}$; and
   a folate tracer labeled with radioiodine and a vitamin B$_{12}$ tracer labeled with radiocobalt.

2. The reagents of claim 1 wherein the folate and vitamin B$_{12}$ binders are in admixture with each other to provide a dual binder, separate from the folate tracer and the vitamin B$_{12}$ tracer.

3. The reagents of claim 1 wherein the folate and vitamin B$_{12}$ tracers are in admixture with each other to provide a dual tracer, separate from the folate binder and vitamin B$_{12}$ binder.

4. The reagents of claim 1 wherein the radioiodine is $^{125}$I.

5. The reagent kit of claim 1 further containing an adsorbent material for effecting said separation of bound and unbound portions.

6. The reagent kit of claim 5 wherein said adsorbent material comprises dextran-coated charcoal.

7. The reagent kit of claim 5 wherein said adsorbent material comprises dextran-coated charcoal.

8. The reagent kit of claim 1 wherein said binder for the folate comprises folate binder from bovine milk.

9. The reagent kit of claim 1 wherein said folate tracer is $\alpha$-(pteroylglutamyl)-$^{125}$I-L-tyrosine.

10. The reagent kit of claim 1 wherein said vitamin B$_{12}$ tracer is vitamin B$_{12}$[$_{57}$Co].

11. The reagent kit of claim 1 wherein said binder for the vitamin B$_{12}$ comprises hog intrinsic factor.

12. Reagents for use in effecting a simultaneous assay for folate and vitamin B$_{12}$ in a sample containing both substances but free of endogenous binder therefor, wherein said sample is contacted at a pH of at least 7.0 with a binder for the folate, a binder for the vitamin B$_{12}$, a folate tracer labeled with a first radioactive isotope, and a vitamin B$_{12}$ tracer labeled with a second radioactive isotope different from the first radioactive isotope different from the first radioactive isotope and the radioactivity of at least one of the bound and unbound portions is counted to determine both folate tracer and vitamin B$_{12}$ tracer, said reagents comprising:
   a binder for the folate and a binder for the vitamin B$_{12}$;
   a folate tracer labeled with a first radioactive isotope and a vitamin B$_{12}$ tracer labeled with a second radioactive isotope different from said first radioactive isotope; and
   a buffer for maintaining said sample at a pH of at least 7.0 during said contacting.

13. The reagents of claim 12 wherein the folate and vitamin B$_{12}$ binders are in admixture with each other to provide a dual binder, separate from the folate tracer and the vitamin B$_{12}$ tracer.

14. The reagent kit of claim 13 wherein said buffer is capable of maintaining said sample at a pH of at least 9.0 and no greater than 9.6 during said contacting.

15. The reagent kit of claim 14 wherein said buffer is capable of maintaining said sample at a pH of from 9.2 to 9.4 during said contacting.

16. The reagents of claim 12 wherein the folate and vitamin $B_{12}$ tracers are in admixture with each other to provide a dual tracer separate from the folate binder and the vitamin $B_{12}$ binder.

17. The reagent kit of claim 12 wherein the vitamin $B_{12}$ is labeled with $^{57}Co$.

18. The reagent kit of claim 17 wherein the folate tracer is a radioiodinated folic acid.

19. The reagent kit of claim 18 wherein the folate tracer is folic acid in which a carboxyl group of the glutamyl moiety is substituted with a member selected from the group consisting of radioiodinated histidyl, radioiodinated tyramyl, radioiodinated histamyl and radioiodinated tyrosyl.

20. The reagent kit of claim 19 wherein the radioiodine is $^{125}I$.

21. The reagent kit of claim 20 wherein said member is $^{125}I$-L-tyrosyl.

22. The reagent kit of claim 18 wherein the folate tracer is folic acid in which a carboxyl group of the glutamyl moiety is substituted with a substituent which includes a radioiodinated phenol or imidazole.

23. The reagent kit of claim 12 further containing an adsorbent material for effecting said separation of bound and unbound portions.

24. The reagent kit of claim 12 wherein said buffer comprises sodium borate and potassium cyanide.

25. The reagent kit of claim 12 wherein said binder for the folate comprises folate binder from bovine milk.

26. The reagent kit of claim 12 wherein said folate tracer is $\alpha$-(pteroylglutamyl)-$^{125}I$-L-tyrosine.

27. The reagent kit of claim 12 wherein said vitamin $B_{12}$ tracer is vitamin $B_{12}[^{57}Co]$.

28. The reagent kit of claim 12 wherein said binder for the vitamin $B_{12}$ comprises hog intrinsic factor.

29. Reagents for use in effecting a simultaneous assay for folate and vitamin $B_{12}$, comprising:
a binder for the folate and a binder for the vitamin $B_{12}$; and
a folate tracer labeled with a first radioactive isotope and vitamin $B_{12}$ tracer labeled with a second radioactive isotope different from the first radioactive isotope, whereby a simultaneous assay for folate and vitamin $B_{12}$ can be effected by using said reagents in a sample containing both folate and vitamin $B_{12}$.

30. The reagents of claim 29 wherein the folate and vitamin $B_{12}$ binders are in admixture with each other to provide a dual binder separate from the folate tracer and the vitamin $B_{12}$ tracer.

31. The reagents of claim 29 wherein the folate and vitamin $B_{12}$ tracers are in admixture with each other to provide a dual tracer separate from the folate binder and the vitamin $B_{12}$ binder.

32. The reagents of claim 29 wherein the folate tracer is radioiodine labeled folic acid and the vitamin $B_{12}$ tracer is radiocobalt labeled vitamin $B_{12}$.

33. The reagent kit of claim 29 wherein said buffer means is capable of maintaining said sample at a pH of at least 9.0 and no greater than 9.6 during said heating and contacting.

34. The reagent kit of claim 29 wherein said folate tracer is $\alpha$-(pteroylglutamyl)-$^{125}I$-L-tyrosine.

35. The reagent kit of claim 32 wherein the folic acid is labeled with a member selected from the group consisting of radioiodinated tyramyl, radioiodinated histamyl and radioiodinated histidyl, said member being substituted on a carboxyl group of the glutamyl moiety.

36. The reagent kit of claim 35 wherein said buffer means is capable of maintaining said sample at the same pH during both heating and subsequent contacting.

37. The reagent kit of claim 36 wherein the $\alpha$ carboxyl group of folic acid is substituted with said member.

38. The reagent kit of claim 37 wherein said member is $^{125}I$-L-tyrosyl.

39. The reagent kit of claim 32 wherein said buffer means is capable of maintaining said sample at a pH of from 9.2 to 9.4 during said heating and contacting.

40. The reagent kit of claim 39 wherein the folic acid is labeled with a member selected from the group consisting of radioiodinated tyrosyl, radioiodinated tyramyl, radioiodinated histamyl and radioiodinated histidyl, said member being substituted on a carboxyl group of glutamyl moiety.

41. The reagent kit of claim 40 wherein said member is L-tyrosyl.

42. The reagent kit of claim 41 wherein the $\alpha$-carboxyl group of folic acid is substituted with said member.

43. The reagent kit of claim 29 further containing an adsorbent material for effecting said separation of bound and unbound portions.

44. The reagent kit of claim 43 wherein said adsorbent material comprises dextran-coated charcoal.

45. The reagent kit of claim 29 wherein said binder for the folate comprises folate binder from bovine milk.

46. The reagent kit of claim 29 wherein said vitamin $B_{12}$ tracer is vitamin $B_{12}[^{57}Co]$.

47. The reagent kit of claim 29 wherein said binder for the vitamin $B_{12}$ comprises hog intrinsic factor.

48. A reagent kit comprising separate reagents for use in effecting a simultaneous assay for folate and vitamin $B_{12}$ comprising:
a dual tracer comprising an admixture of a folate tracer labeled with a first radioactive isotope and a vitamin $B_{12}$ tracer labeled with a second radioactive isotope different from said first isotope; and
a dual binder comprising an admixture of a binder for folate and a binder for vitamin $B_{12}$.

49. A reagent kit comprising separate reagents for use in effecting a simultaneous assay for folate and vitamin $B_{12}$ comprising:
a dual tracer comprising an admixture of a folate tracer labeled with a first radioactive isotope and a vitamin $B_{12}$ tracer labeled with a second radioactive isotope different from said first isotope; and
a dual binder comprising an admixture of a binder for folate and a binder for vitamin $B_{12}$; and
a plurality of dual standards, each comprising a premeasured standard for folate and a premeasured standard for vitamin $B_{12}$.

50. A reagent kit comprising initially uncombined reagents for use in effecting a simultaneous assay for folate and vitamin $B_{12}$ in a sample containing both substances associated with endogenous binders therefor, wherein said sample is heated in the presence of a reducing agent which maintains reduced folate without adversely affecting vitamin $B_{12}$ at a pH of at least 7.0, said heating being effected to a temperature to heat release folate and vitamin $B_{12}$ from their endogenous binders; then the sample is contacted at a pH of at least 7.0 with a binder for the folate, a binder for the vitamin $B_{12}$, a folate tracer labeled with a first radioactive isotope, and a vitamin $B_{12}$ tracer labeled with a second radioactive isotope different from the first radioactive isotope; then portions of the folate and vitamin $B_{12}$ bound to the binders are separated from the unbound portions of folate and vitamin $B_{12}$; and thereafter the radioactivity of at least one of the bound and unbound portions is counted to determine both folate tracer and vitamin $B_{12}$ tracer, said reagents comprising:

(1) a reducing agent capable of maintaining reduced folate without adversely affecting vitamin $B_{12}$ at said heat release temperature;

(2) a dual binder comprising an admixture of a binder for the folate and a binder for the vitamin $B_{12}$;

(3) a folate tracer labeled with a first radioactive isotope and a vitamin $B_{12}$ tracer labeled with a second radioactive isotope different from said first radioactive isotope; and (4) a buffer for maintaining said sample at a pH of at least 7.0 during said heating and contacting.

51. The a reagent kit of claim 50 wherein said buffer is capable of maintaining said sample at a pH of at least 9.0 and no greater than 9.6 during said heating and contacting.

52. The a reagent kit of claim 50 wherein said buffer means is capable of maintaining said sample at the same pH during both heating and subsequent contacting.

53. The a reagent kit of claim 50 and an adsorbent material for effecting said separation of bound and unbound portions.

54. The a reagent kit of claim 53 wherein said adsorbent material comprises dextran-coated charcoal.

55. The a reagent kit of claim 50 wherein said buffer means comprises sodium borate and potassium chloride.

56. The a reagent kit of claim 50 wherein said reducing agent comprises dithiothreitol.

57. The a reagent kit of claim 50 wherein said binder for the folate comprises folate binder from bovine milk.

58. The a reagent kit of claim 50 wherein said folate tracer is -(pteroylglutamyl)-$^{125}$I-L-tyrosine.

59. The a reagent kit of claim 50 wherein said vitamin $B_{12}$ tracer is vitamin $B_{12}[^{57}Co]$.

60. The a reagent kit of claim 50 wherein said binder for the vitamin $B_{12}$ comprises hog intrinsic factor.

61. The a reagent kit of claim 50 wherein said folate tracer and said vitamin $B_{12}$ tracer are in admixture and together present a dual tracer.

62. The a reagent kit of claim 50 wherein said first isotope is $^{125}$I.

63. The a reagent kit of claim 50 wherein said second isotope is $^{57}$Co.

64. The a reagent kit of claim 50 wherein said buffer is capable of maintaining said sample at a pH of at least 9.0 and no greater than 9.6 during said contacting.

65. The a reagent kit of claim 64 wherein said buffer is capable of maintaining said sample at a pH of from 9.2 to 9.4 during said contacting.

66. The reagent kit of claim 29 wherein said buffer means comprises sodium borate and potassium cyanide.

67. The reagent kit of claim 29 wherein said reducing agent comprises dithiothreitol.

* * * * *